US006114596A

United States Patent [19]
Nayak et al.

[11] Patent Number: 6,114,596
[45] Date of Patent: *Sep. 5, 2000

[54] BREATHABLE DISPOSABLE SANITARY PRODUCT CONSTRUCTION AND BARRIER SHEET

[75] Inventors: Rahul K. Nayak, Stuarts Draft; Roe Clyde Allen, Crozet, both of Va.; C. Allen Bodford, Atlanta, Ga.

[73] Assignee: Polybond, Inc., Waynesboro, Va.

[*] Notice: This patent is subject to a terminal disclaimer.

[21] Appl. No.: 08/720,631

[22] Filed: Oct. 2, 1996

Related U.S. Application Data

[63] Continuation-in-part of application No. 08/552,727, Nov. 3, 1995, Pat. No. 5,643,239.

[51] Int. Cl.[7] ............................. A61F 13/15; A61F 13/20
[52] U.S. Cl. ......................... 604/370; 604/365; 604/367
[58] Field of Search .................................. 604/365, 367, 604/370, 383, 384

[56] References Cited

U.S. PATENT DOCUMENTS

| | | | |
|---|---|---|---|
| 4,704,116 | 11/1987 | Enloe . | |
| 4,828,556 | 5/1989 | Braun et al. | 604/365 |
| 4,834,740 | 5/1989 | Suzuki et al. . | |
| 5,292,316 | 3/1994 | Suzuki . | |
| 5,492,751 | 2/1996 | Butt, Sr. et al. . | |
| 5,558,658 | 9/1996 | Menard et al. | 604/382 |
| 5,643,239 | 7/1997 | Bodford et al. | 604/370 |

FOREIGN PATENT DOCUMENTS

WO94/23107   10/1994   WIPO .

OTHER PUBLICATIONS

ASTM D737–75
Laboratory Test Method: Rising Water Column.
V.M. Desai and V.D. Athawale, "Water Resistant–Breathable Hydrophilic Polyurethane Coatings," Journal of Coated Fabrics, vol. 25 –Jul. 1995.
"Melt Blown Production," J and M Laboratories, Inc.

*Primary Examiner*—Mark O. Pollutta
*Attorney, Agent, or Firm*—Juettner Pyle & Piontek

[57] ABSTRACT

A breathable diaper, feminine hygiene, or like disposable sanitary product construction having a cloth-like outer surface and including a plurality of materials from the skin-facing side outwardly, a topsheet, a core, an optional barrier, and a backsheet. The topsheet is formed of liquid- and vapor-permeable hydrophilic material, and the core is formed of highly absorbent material disposed outwardly of the topsheet for absorbing liquid received through the topsheet. The core has an inner surface in liquid communication the said topsheet and an outer surface. The optional barrier is formed of a multilayer non-woven material which is hydrophobic and vapor-permeable for limiting the outward escape of liquid therethrough while enabling the outward escape of heat and water vapor therethrough. The barrier has a base disposed adjacent the core outer surface. The backsheet is formed of a multilayer non-woven material which is hydrophobic and vapor permeable for limiting the outward escape of liquid therethrough while enabling the outward escape of heat and water vapor therethrough. The backsheet is disposed at least partially as an outer surface of the diaper. At least one of the optional barrier material and the backsheet material has at least two meltblown layers.

54 Claims, 11 Drawing Sheets

BREATHABLE DISPOSABLE SANITARY PRODUCT CONSTRUCTION AND BARRIER SHEET

CROSS-REFERENCE TO RELATED APPLICATION

This is a continuation-in-part of U.S. patent application Ser. No. 08/552,727, filed Nov. 3, 1995 now U.S. Pat. No. 5,643,239.

BACKGROUND OF THE INVENTION

The present invention relates to breathable diapers, feminine hygiene or like disposable sanitary product constructions, and more particularly to such a construction which is breathable and has an outer or backsheet surface which is cloth-like.

Disposable diapers for infants and incontinent older people are a major industry and, as such, constitute a crowded art, competitively speaking. In general, such sanitary product constructions comprise, from the skin-facing side outwardly, an inner topsheet (also called a cover or front sheet) which is liquid-permeable to facilitate entry of the fluid exudate from the wearer into the construction, a core of highly absorbent material for absorbing liquid received through the topsheet, and an outer backsheet formed of a vapor- and liquid-impermeable plastic to eliminate leakage of fluid from the diaper.

Such diapers have not proven to be entirely satisfactory. While the inner topsheet is typically in the form of a cloth-like material having a soft hand (which is correctly perceived as being comfortable for the baby to have adjacent to its skin), the outer backsheet plastic presents a rather cold, clammy surface which is at least perceived of as inhospitable and uncomfortable for the baby's skin. Further, the feel of the plastic backsheet to the parent or caregiver is inhospitable and uncomfortable in comparison to conventional cloth diapers. While the outer backsheet is less likely to come into contact with the baby's skin then the inner topsheet, the plastic backsheet is still perceived of as a negative and presumably discourages potential customers for disposable diapers in favor of cotton diapers.

Further, the plastic backsheet is impervious not only to liquid, but generally to heat and water vapor as well. Accordingly, the moisture vapor and the heat generated by the bodily exudate trapped within the diaper lead to conditions adjacent the wearer's skin which promote skin irritation, infection, and the like.

While the plastic backsheet is generally effective in precluding the passage of bodily exudate outwardly therethrough where the highly absorbent core is present, it is not efficient in preventing side leakage—that is, lateral leakage of liquids from the opposed side portions of the core sidewards between the leg gathers of the backsheet and the baby's skin. The obvious solution to the problem—tightening of the leg gathers—in turn presented problems in terms of the comfort of the baby, skin irritation, etc.

Accordingly, it is an object of the present invention to provide in one preferred embodiment a breathable diaper, feminine hygiene or like disposable sanitary product construction which has a cloth-like outer backsheet surface.

Another object is to provide in one preferred embodiment such a construction which is breathable to enable the escape of water vapor and heat therethrough.

A further object is to provide in one preferred embodiment such a construction which efficiently limits side leakage.

It is also an object of the present invention to provide a preferred embodiment of a disposable sanitary product construction having a backsheet surface which is cloth-like and of good hand, is breathable, and affords an efficient system for limiting side leakage.

It is a further object to provide such a construction which is simple and inexpensive to manufacture.

SUMMARY OF THE INVENTION

It has now been found that the above and related objects of the present invention are obtained in a breathable diaper, feminine hygiene or like disposable sanitary product construction having a cloth-like outer surface. The construction includes a plurality of materials comprising, from the skin-facing side outwardly, a topsheet, a core, an optional barrier and a backsheet. The topsheet is formed of liquid- and vapor-permeable hydrophilic material. The core is formed of highly absorbent material for absorbing fluid received through the topsheet. The core has an inner surface in fluid communication with the topsheet, an outer surface and two lateral side surfaces. The optional barrier is formed of a multilayer non-woven material which is hydrophobic and vapor permeable for limiting the outward escape of liquid therethrough while enabling the outward escape of heat and water vapor therethrough. The barrier has a base disposed adjacent the core outer surface. The backsheet is formed of a multilayer non-woven material which is hydrophobic and vapor permeable for limiting the outward escape of liquid therethrough while enabling the outward escape of heat and water vapor therethrough. The backsheet is disposed at least partially outwardly of the barrier base and as the outer surface of the construction.

In a preferred embodiment, the backsheet and/or barrier material is SM, a two-layer spunbond-meltblown non-woven fabric formed of a spunbond layer and a meltblown layer. In an optimal embodiment, the backsheet and/or barrier material is SMS, a three-layer spunbond-meltblown-spunbond non-woven fabric formed of two spunbond layers and a meltblown layer disposed intermediate the spunbond layers and bonding them together. The construction may include an additive or coating which increases the hydrophobicity of the material. The liquid contact angle of the non-woven fabric can be suitably adjusted to improve the hydrohead.

The topsheet may be a one-layer spunbond non-woven material, a liquid-distributing material, or a two-layer fabric formed of an inner layer of a liquid and vapor-permeable hydrophilic non-woven material and an outer layer of a liquid-distributing material. Preferably the barrier base is thicker than the barrier flanges to further limit the outward escape of liquid therethrough. A portion of the backsheet material may include elastic material such that, in use, a portion of the backsheet material is gathered about the legs of the user.

The construction preferably includes a hydrophobic enhancer formed of a multilayer non-woven material which is hydrophobic and vapor-permeable for limiting the outward escape of liquid therethrough while enabling the outward escape of heat and water vapor therethrough. The hydrophobic enhancer is disposed at least partially outwardly of the barrier base and inwardly of the backsheet. The hydrophobic enhancer is preferably SM or SMS. The hydrophobic enhancer may be a hydrophobic coating disposed adjacent an inner surface of the backsheet, the coating being polymeric, but cracked or fractured to provide breathability thereto. The cracked coating is preferably an ethyl vinyl acetate (EVA) extrusion having cracks or fractures sufficient to provide breathability thereto.

The present invention further encompasses a new barrier sheet comprising a multilayer non-woven material having a cloth-like outer surface and which is hydrophobic and vapor-permeable for limiting the outward escape of liquid therethrough while enabling the outward escape of heat and water vapor therethrough. The barrier sheet material has at least two meltblown layers and is one of: (i) a three-layer spunbond-meltblown-meltblown non-woven fabric formed of a spunbond layer and a plurality of meltblown layers disposed on one side of the spunbond layer, and (ii) a four-layer spunbond-meltblown-spunbond-meltblown non-woven fabric formed of two spunbond layers and two meltblown layers, one of the meltblown layers being disposed intermediate the two spunbond layers and bonding them together.

In a preferred embodiment the barrier sheet material includes a relatively coarse meltblown layer formed of fibers having a diameter of 3–5 microns (average 4) and a relatively fine meltblown layer formed of fibers having a diameter of 0.5–1.5 microns (average 1.0), the relatively fine meltblown layer being disposed on one side of the relatively coarse meltblown layer. The barrier sheet material has the exterior meltblown layer formed from a polymer selected from the group consisting of paraffin wax, polypropylene, and ethyl vinyl acetate copolymer, and the spunbond and interior meltblown layers thereof formed of polypropylene.

The present invention finally encompasses any of the aforementioned disposable sanitary product constructions using the new barrier sheet as the barrier, the backsheet or both.

BRIEF DESCRIPTION OF THE DRAWING

The above and related objects, features, and advantages of the present invention will be more fully understood by reference to the following detailed description of the presently preferred, albeit illustrative, embodiments of the present invention when taken in conjunction with the accompanying drawing wherein.

DETAILED DESCRIPTION OF THE PREFERRED EMBODIMENTS

Figure 1:
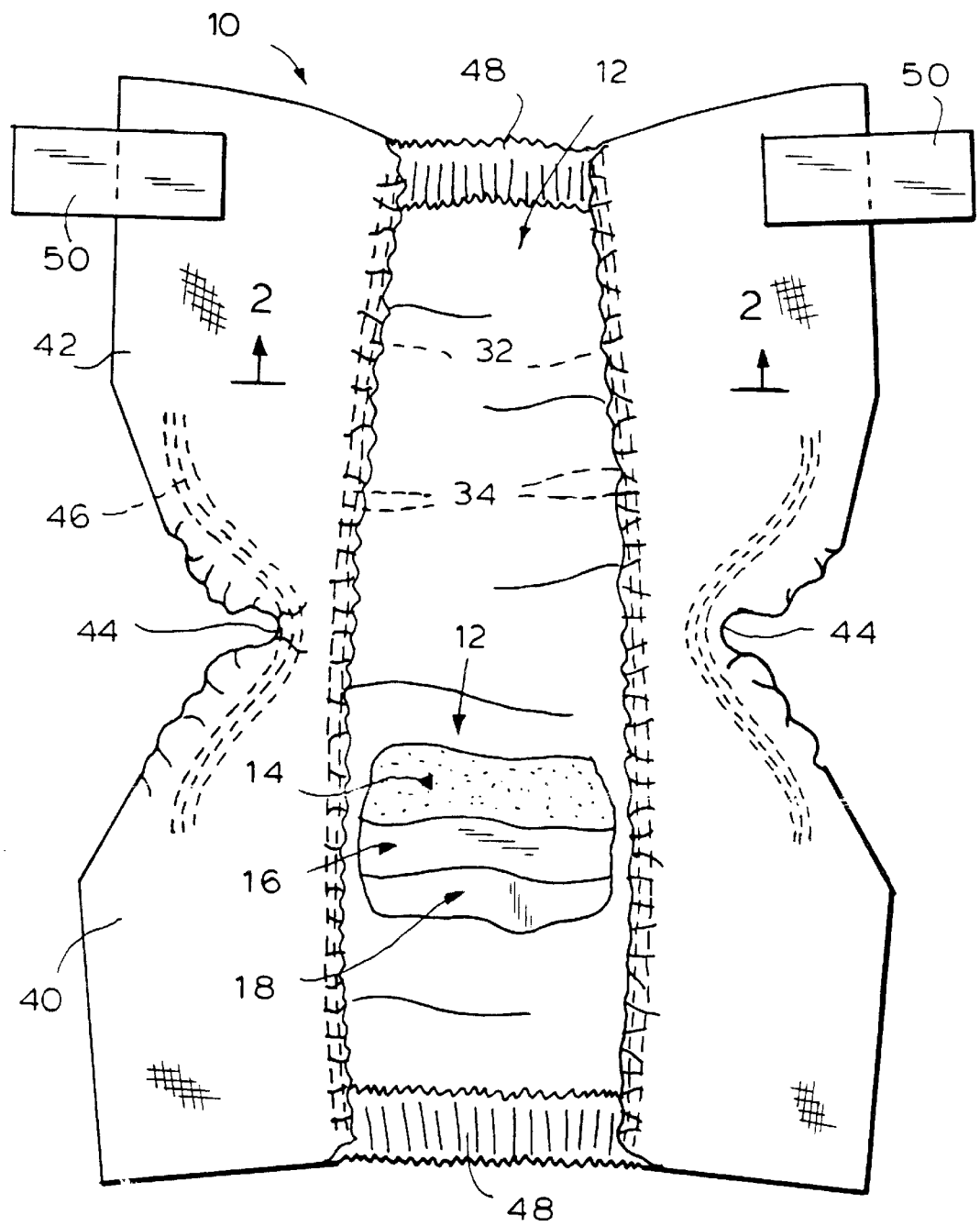
FIG. 1 is a top plan view of a simple embodiment of a diaper according to the present invention, with successive portions thereof being removed to reveal details of internal construction.
Figure 2:
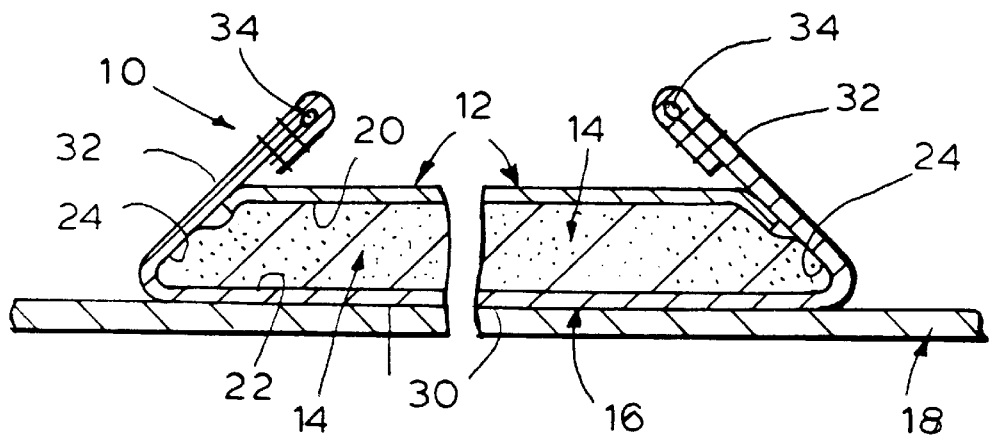
FIG. 2 is a sectional view thereof taken along the line 2—2 of FIG. 1.

Referring now to the drawing, and in particular to FIGS. 1 and 2 thereof, therein illustrated is a simple embodiment of a breathable diaper according to the present invention, generally designated by the reference numeral 10. As will be appreciated by those skilled in the art, the principles of the disposable sanitary product construction may be used for other disposable sanitary products such as feminine hygiene products, e.g., catamenial pads and the like, although typically the manner of securing the construction in place on the wearer's body will differ.

The construction 10 includes a plurality of materials comprising, from the skin-facing side outwardly, a topsheet generally designated 12, a core generally designated 14, a barrier generally designated 16, and a backsheet generally designated 18.

As is typical in these constructions, the topsheet 12 is formed of a liquid- and vapor-permeable hydrophilic material. For example, a preferred topsheet is formed of a one-layer, spunbond, non-woven fabric, with a soft, cloth-like surface for contact with the wearer's skin. While various liquid- and vapor-permeable hydrophilic materials may be used for the topsheet 12, a satisfactory diaper must be capable of providing the cloth-like inner surface affording good hand (e.g., softness).

Alternatively, the topsheet 12 may be formed of a liquid-distributing material, preferably one offering the same soft cloth-like feel as the spunbond topsheet. The liquid-distributing material performs a wicking service, drawing the liquid of the exudate away from the wearer and spreading it over a greater area of the topsheet 12 for transmission to the core 14.

Figure 4:
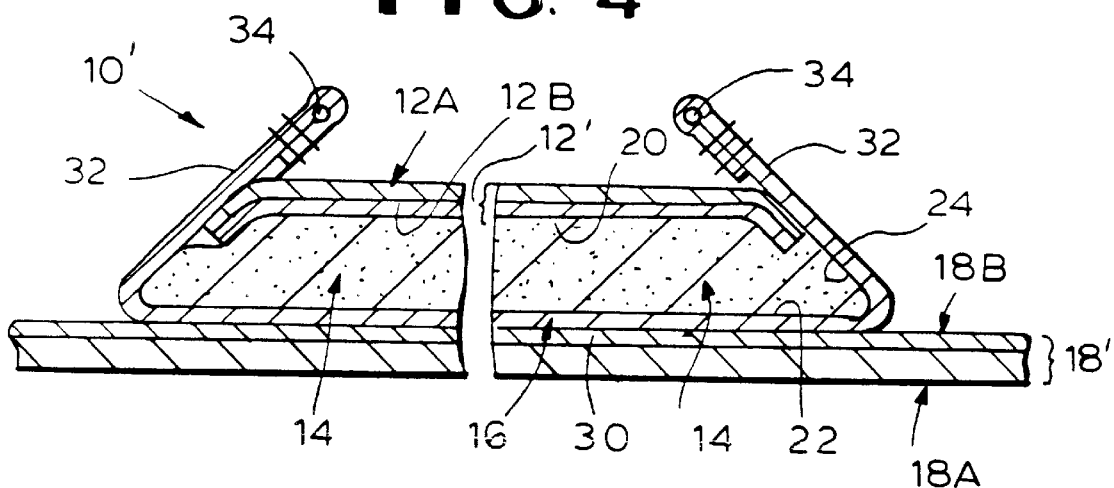
FIG. 4 is a sectional view thereof taken along the line 4—4 of FIG. 3.
Figure 3:
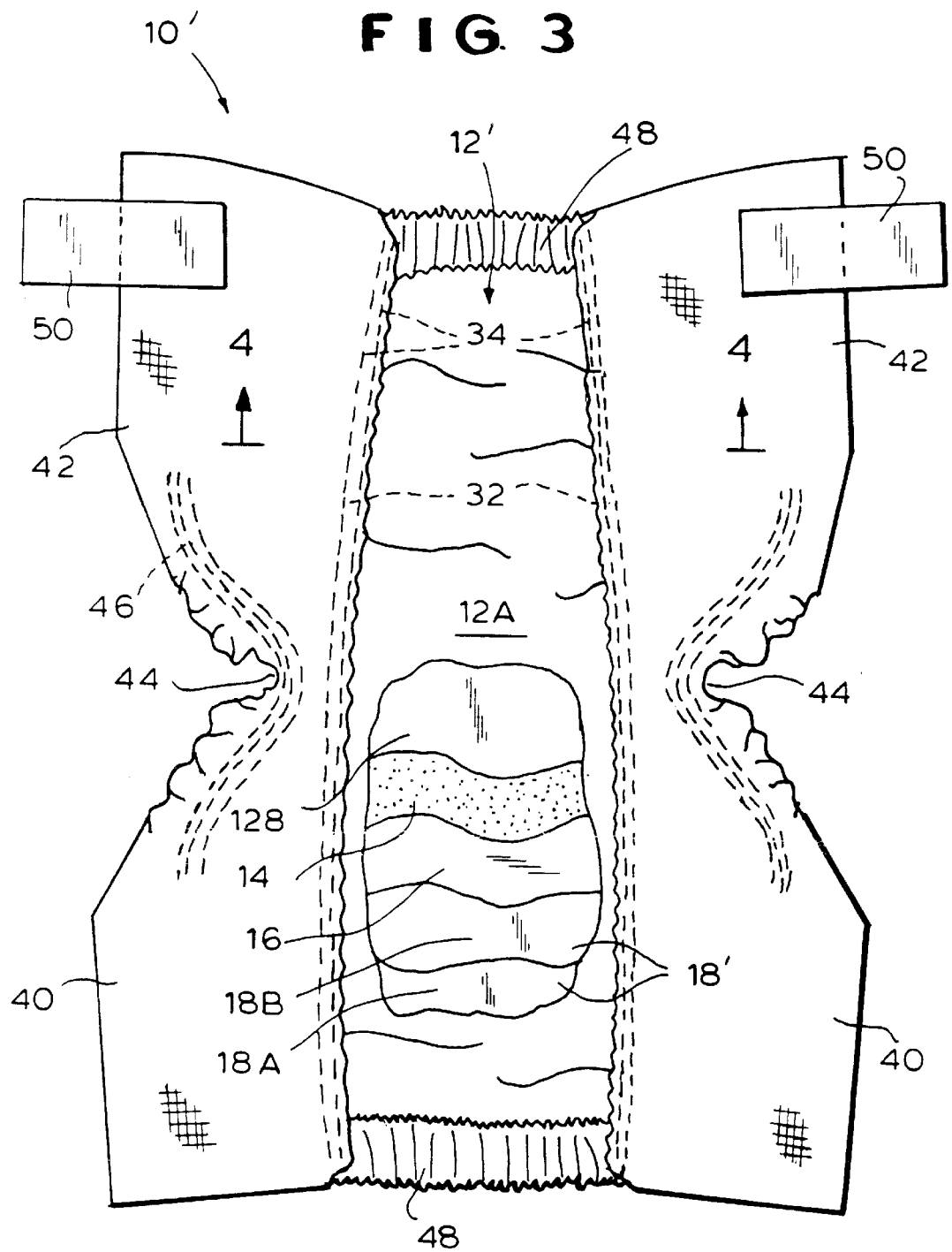
FIG. 3 is a top plan view of a more complex embodiment with successive portions thereof being removed to reveal details of internal construction.

In the preferred, more complex embodiment 10' of the diaper illustrated in FIGS. 3 and 4, the topsheet 12' is a two-layer fabric formed of an inner layer 12A of a liquid- and vapor-permeable, hydrophilic, non-woven material, and an outer layer 12B formed of a liquid-distributing material. Thus the preferred topsheet 12' is not only a liquid- and vapor-permeable hydrophilic material, but also a fluid-distributing material.

The topsheet 12 may comprise any of the materials heretofore employed for topsheets, e.g., spunbonded, polyester or polypropylene fibers, various non-woven fabrics, etc. having the desired wet and dry strengths as well as the liquid and vapor-permeability and hydrophilic characteristics earlier mentioned.

Referring now to FIGS. 1–4, in both embodiments 10 and 10', the core 14 is formed of a highly absorbent material and is disposed outwardly of the topsheet 12, 12' for absorbing liquid received through the topsheet. The core 14 has an inner surface 20 in liquid communication with the topsheet, an outer surface 22, and two lateral side surfaces 24, 24. (Typically, the core 14 extends longitudinally along the crotch, with the lateral side surfaces thereof being generally parallel to that longitudinal axis.) The core may be composed of any of the absorbent materials heretofore employed for that purpose in the diaper art, e.g., wood pulp or fluff, absorbent cotton fibers, polyester or polypropylene and the like, including mixtures thereof. Preferably, the core 14 is formed of a superabsorbent or like material which wicks the liquid received from the topsheet through and away from the topsheet, so that the topsheet generally presents a relatively dry inner surface to the wearer. As highly absorbent materials suitable for the core are well known in the conventional diaper, feminine hygiene and like sanitary product constructions art, further details thereof need not be provided herein.

The barrier 16 is disposed partially outwardly of the core 14 and is formed of a multilayer, non-woven material which is hydrophobic and vapor-permeable for limiting the outward escape of liquid therethrough, while enabling the outward escape of heat and water vapor therethrough. It has been found that the heat and humidity released by the accumulated body exudates, such as urine and feces, promote the irritation and itching which frequently develops when conventional disposable diapers are used. The barrier 16 of the present invention enables the heat and water vapor to escape outwardly from the core 14, through the barrier 16 and then further outwardly while at the same time limiting the outward escape of liquid (e.g., urine, blood, etc.) therethrough. The non-woven material may be spunbond, carded, spun-laced, meltblown or the like. A chemical finish may be applied in order to enhance its ability to repel specific liquids. The preferred materials are polyethylene, polypropylene, and the like.

Figure 5:
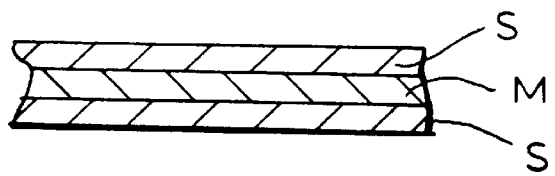
FIG. 5 is a fragmentary sectional view of a multilayered non-woven material—namely, a spunbond-meltblown-spunbond material.

The barrier material 16 is preferably SM or optimally SMS. SM is a two-layer spunbond-meltblown non-woven fabric formed of a spunbond layer and a meltblown layer. When SM is used, the meltblown layer is typically the inner layer. Referring now to FIG. 5, SMS is a three-layer, spunbond-meltblown-spunbond non-woven fabric formed of two spunbond layers S and a meltblown layer M disposed intermediate the spunbond layers and bonding them together. The spunbond and meltblown layers are typically formed of the same composition—preferably either polyethylene or propylene—although different compositions formed of other natural or synthetic materials may be used. Typically, the meltblown material is similar to the spunbond material, both fibers being essentially continuous, except that the fiber diameters are substantially smaller (such that the meltblown material by itself lacks tenacity and cannot be used by itself). Multilayer non-woven materials which are hydrophobic and vapor-permeable (i.e., water vapor-permeable) are well known in the art, and accordingly it is not deemed necessary to set forth herein further details thereof. It will be appreciated, however, that the layers forming the SM or SMS material may contain conventional additives to increase the hydrophobicity of the material, or even a coating, so long as the aforementioned desirable properties of the material are that adversely affected.

When the diaper is in use, as illustrated in FIG. 2, barrier 16 is U-shaped in cross section and has a base 30 at least partially disposed adjacent the outer surface 22 of the core 14 and a pair of flanges 32 upstanding from the base 30. Each of the flanges 22 extends inwardly (towards the topsheet 12) closely adjacent to a respective one of the core lateral side surfaces 24.

Even after distribution over the major face of the core 14 by a liquid-distributing topsheet 12, 12', the liquid passing from the core 14 to the barrier 16 still tends to bunch at the center of the core 14 rather than at the lateral sides 24 thereof. Accordingly, preferably the barrier base 30 is thicker than the barrier flanges 32, thereby to further limit the outward escape of liquid through the barrier base 30.

A portion of the barrier flanges 32, especially adjacent the free ends thereof, includes elastic or other biasing material 34 such that, when worn, a portion of the barrier flanges 32 are gathered about the legs of the user, thereby to prevent the escape of liquid laterally from the diaper. The elastic material 34 may be embedded in a folded-over free end of the barrier flanges 32, as illustrated, or it may simply be glued or stitched thereto. Thus, when the diaper 10 or 10' is tautly stretched out, as illustrated in FIGS. 1 and 3, the barrier flanges 32 lay flat over the topsheet 12 or 12' and core 14 while, when the diaper is worn as illustrated in FIGS. 2 and 4, the barrier flanges 32 stand upright to prevent the lateral escape of liquid exudate from the diaper. Optionally the free ends of the barrier flanges 32 may be secured to the lateral edges of the top sheet 12 to limit liquid leakage therebetween.

It will be appreciated that the core 14 is encapsulated on all four sides: by the topsheet 12, 12' on its inner surface 20, the barrier base 30 on its outer surface 22, and the barrier flanges 32 on its lateral sides 24.

The backsheet 18, like the barrier 16, is formed of a multilayer non-woven material which is hydrophobic and vapor-permeable for limiting the outward escape of liquid therethrough while enabling the escape of heat and water vapor therethrough. The preferred backsheet material is a two-layer SM or a three-layer SMS, as described above. The backsheet 18 is at least partially disposed outwardly of the barrier base 30. Any liquid which passes out of the core 14 and through the barrier 16 encounters the backsheet 18, which further limits its outward escape.

The backsheet 18 is typically formed in the configuration of a conventional diaper having a front portion 40, a rear portion 42 and a crotch portion 44 therebetween. The crotch portion 44 typically includes elastic threads 46 for gathering the backsheet 18 around the legs of the wearer. The central longitudinal portion of the backsheet 18 may define gathers 48 at its opposed waist ends to assist in shaping the diaper and keeping the various components thereof in place—for example, by stitching therethrough to drape the gathers 48.

Conventional mechanical fasteners 50, such as adhesive or VELCRO (trademark of VELCRO USA Inc.) tabs, are permanently fastened to the rear portion 42 of backsheet 18 so that they may be releasably attached to the front portion 40 when the diaper is placed on the wearer. The pair of conventional fasteners in the waist area permit releasably securing or refastening of the opposed ends of the backsheet 18 together around the waist of the wearer where the diaper is folded to engage the front and back of the body. The fasteners may employ refastenable pressure-sensitive adhesive and may be elastic in nature.

The presence of a backsheet 18 formed of a multilayer, non-woven material enables the outer surface of the diaper to have an outer surface with a cloth-like feel similar to that of a conventional cloth diaper. Accordingly, a potential purchaser of the diaper will be under the impression that he/she is affording twice the comfort and protection of a conventional diaper because a soft, cloth-like material forms both the topsheet 12 and the backsheet 18.

In the preferred, albeit more complex, embodiment 10' of the present invention illustrated in FIGS. 3 and 4, the construction 10' includes the backsheet 18' defining diaper outer surface 18A and a hydrophobic enhancer 18B formed of a multilayer, non-woven material. The multilayer, non-woven material of enhancer 18B is hydrophobic and vapor-permeable for limiting the outward escape of liquid therethrough while enabling the outward escape of heat and water vapor therethrough. The preferred enhancer material is a two-layer SM or a three-layer SMS as described above.

Preferably the hydrophobic enhancer 18B is at least partially disposed outwardly of the barrier base 30 and inwardly of the backsheet 18A. Indeed, the hydrophobic enhancer 18B may simply be a coating disposed adjacent the inner surface of backsheet 18A. The hydrophobic coating is preferably cracked or fractured to provide breathability thereto. Preferred coatings are polymers—e.g., an ethyl vinyl acetate (EVA) extrusion having cracks or fractures sufficient to provide breathability therethrough. It will be appreciated that the presence of the enhancer 18B as either a separate layer or as a coating on the inner surface of backsheet 18A does not detract from the desirable soft feel of the latter.

Liquid exudate escaping from the lateral sides of the core 14 are initially blocked by the barrier 16 and trapped in the U-shaped well 32, 30, 32 of the barrier 16. Even if the liquid exudate escapes the well of the barrier, it is still retained within the diaper by the backsheet 18 or the hydrophobic enhancer 18B and backsheet 18A, depending upon the embodiment of the diaper.

The various materials 12, 14, 16, 18 of diaper 10 or 12A, 12B, 14, 16, 18A, 18B of diaper 10' may be secured together with hot-melt or like adhesives or even simple mechanical or stitching means, as is customary in the diaper art.

The diaper 10, 10' according to the present invention is used in the same manner as a conventional diaper.

Figure 6:
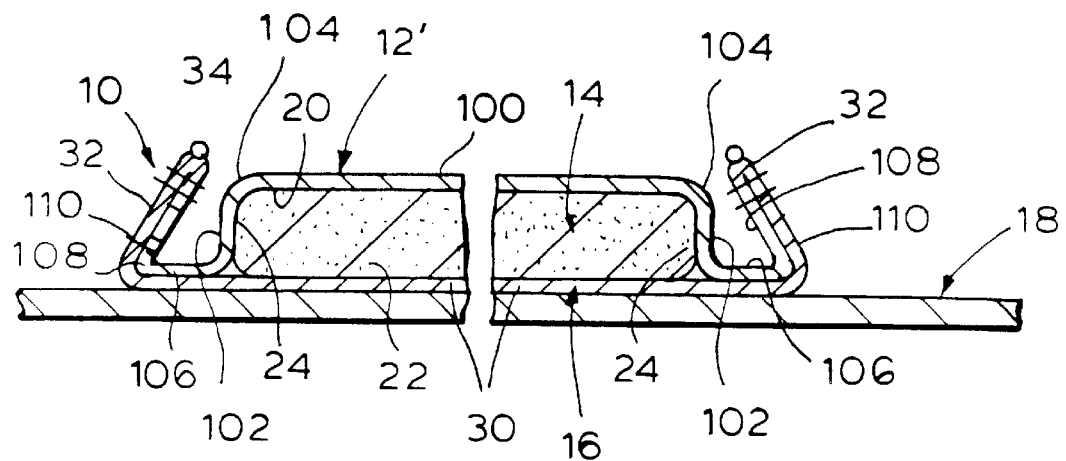
FIG. 6 is a sectional view of a variant of the simple embodiment.
Figure 7:
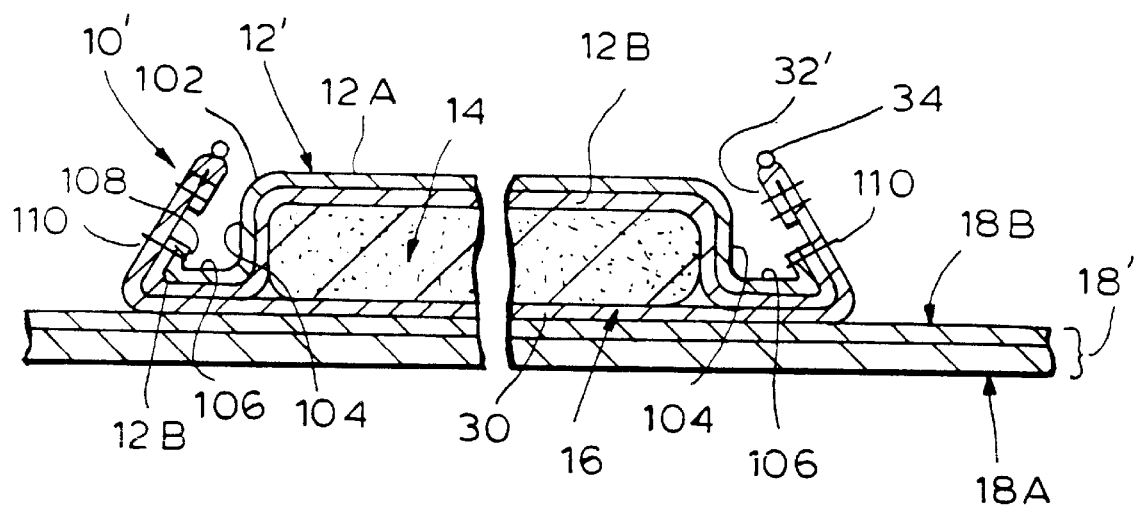
FIG. 7 is a sectional view of a variant of the more complex embodiment.

While the embodiments illustrated in FIGS. 1–4 have the barrier flanges 32 disposed contiguous to the core lateral side surfaces 24, and only optionally secured to the topsheet 12, alternatively the topsheet 12 and the barrier 16 may be directly secured together at a location optionally spaced from core 14. Thus, as illustrated in FIG. 6, the topsheet 12' defines a topsheet base 100 disposed adjacent the core inner surface 20 and a pair of topsheet flanges 102 extending outwardly from the topsheet base 100. The topsheet flanges 102 are U-shaped, each topsheet flange 102 having one leg 104 disposed contiguous to or very closely adjacent to the core lateral side surface 24, the topsheet base 106 being disposed generally parallel to the barrier base 30, and the other topsheet flange leg 108 being secured to the barrier flange 32, as illustrated at 110. As illustrated in FIG. 7, clearly the principles of this variant are equally applicable to a variant of the more complex embodiment illustrated in FIGS. 3 and 4, and, indeed, the configuration of the topsheet flanges and the barrier flanges may be varied substantially as long as each topsheet flange is secured to a respective barrier flange in such a manner as to minimize side leakage.

To summarize, the present invention provides a breathable diaper, feminine hygiene or like disposable sanitary product construction which has a cloth-like outerback sheet surface, is breathable to enable the escape of water vapor and heat therethrough, and efficiently limits side leakage of liquid. The construction is simple and inexpensive to manufacture.

Notwithstanding the foregoing, it has been found that the invention described above can be improved to further preclude the possibility of leakage in the event that the bodily exudate flow is substantial (e.g. in overnight use). This is done without sacrificing the backsheet or barrier/backsheet being vapor-permeable, thereby to enable the outward escape of heat and water vapor therethrough, and the cloth-like outer backsheet surface.

Figure 8:
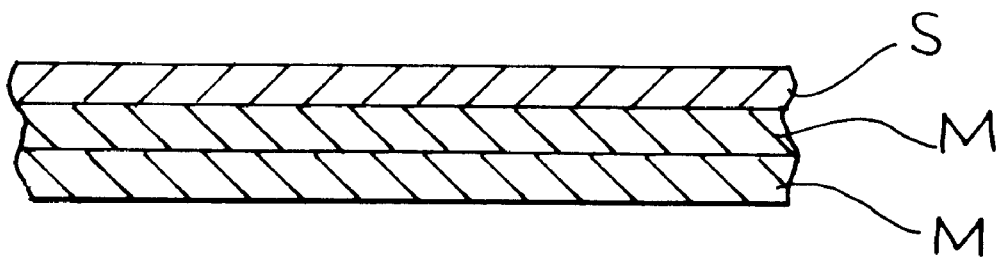
FIG. 8 is a sectional view of an improved SMM barrier sheet according to the present invention.
Figure 9:
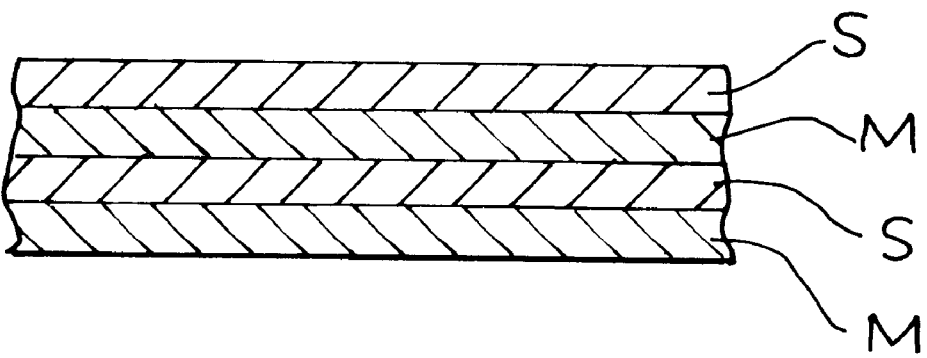
FIG. 9 is a sectional view of an improved SMSM barrier sheet according to the present invention.

Accordingly, a new barrier sheet according to the present invention, generally designated 200, has been developed. The new barrier sheet 200 is preferably SMM or optimally SMSM. Referring now to FIG. 8, SMM is a three-layer spunbond-meltblown-meltblown non-woven fabric formed of a spunbond layer S and two meltblown layers M disposed on one side of the spunbond layer, typically the inner or skin-facing side. Referring now to FIG. 9, SMSM is a four-layer spunbond-meltblown-spunbond-meltblown non-woven fabric formed of two spunbond layers S and two meltblown layers M, one of the meltblown layers M being disposed intermediate the two spunbond layers S and bonding them together. The exterior or add-on meltblown layer M of the new barrier sheet 200 is preferably a polymer selected from the group consisting of paraffin wax, polypropylene, ethyl vinyl acetate copolymer, and polypropylene/ethyl vinyl acetate copolymer. The spunbond layer(s) S and the interior meltblown layer M of the substrate are preferably formed of polypropylene. Of course, different compositions formed of other natural or synthetic materials may be used. A preferred barrier sheet 200 has each layer formed of polypropylene.

It will be appreciated that the exterior meltblown layer M of the new barrier sheet 200 in the SMM or SMSM configurations may include two or even more adjacent M layers, one atop the other. However, more than two M layers adjacent one another is not recommended as the application of the M layers in succession tends to thermally degrade and stiffen the sheet 200.

Interestingly, it has been found that regardless of whether the new barrier sheet 200 is of the SMM or SMSM configuration, it is preferable if the two meltblown layers M differ. More particularly, one of the meltblown layers M (preferably the substrate layer M) should be a relatively coarse meltblown layer formed of fibers having a diameter of 1.0–25 microns, preferably 1.0–15 and optimally 1.5–7 microns, while the other meltblown layer M (preferably the add-on layer M) should be a relatively fine meltblown layer formed of fibers having a diameter of 0.5–6.0 microns, preferably 0.5–4.0 and optimally 0.5–2.0 microns. It is believed that the relatively coarse layer will be formed of fibers having a diameter of 3–5 microns, with an average of about 4 microns, while the relatively fine meltblown layer will be formed of fibers having a diameter of 0.5–1.5 microns, with an average of about 1.0 micron. Both the relatively coarse and relatively fine meltblown layers are typically formed of essentially continuous fibers. Preferably the relatively fine meltblown layer is disposed inwardly (that is, on the skin-facing side of a diaper, toward 18 of FIG. 7), and the relatively coarse layer is disposed outwardly of the fine layer. The fine layer tends to abrade relatively easily and is afforded some protection by the coarse layer. Further the fibers of the relatively fine layer are to some degree supported by the adjacent coarser fiber layer. This is important because the fine fibers are under the "stress" of wearing, motion of the baby, and baby fluid exudates during use.

Referring now to FIGS. 1–7, it will be appreciated by those skilled in the art that the new barrier sheet 200 (whether of SMM or SMSM configuration) may be used as either the barrier 16 (whether with or without the barrier flanges 32) or backsheet 18 of the simple or more complex embodiments described above, thereby replacing the SM or SMS material described above. The new barrier sheet 200 may replace either or both of the materials used in the barrier and backsheet, so that the new and old types of barrier sheet may be employed in the same construction. The new barrier sheet 200 may be used as the backsheet 18 in constructions not having the optional barrier 16.

The thermal bonding of the various layers of the base substrate may occur prior to the application of the add-on meltblown layer. In this case the addition of the add-on meltblown layer may be through a process of web consolidation (such as calendering) without thermal bonding. Preferably, any such calendering will occur below the distortion temperature. However this type of off-line process involves two steps: one to create the base substrate, and one to add the add-on meltblown layer. Accordingly, its costs are somewhat higher than that of a process in which the several components of the base substrate and the one or more components of the add-on meltblown layer are all thermally bonded together in a single step. Thermal bonding is also superior to mere web consolidation as the thermally bonded fibers have a high resistance to being shed off. In those instances where the add-on meltblown layer does not adhere well to the base substrate, an adhesive add-on may be employed between the two components—e.g., a layer of hot-melt adhesive.

The presence of the add-on or exterior meltblown layer in the new SMM or SMSM barrier sheet 200 increases the water impermeability of the substrate (as measured by the hydrostatic head pressure of Method 5514 Federal Test Method STD No. 191-A) while decreasing the air permeability of the substrate (as measured by ASTM D-737-75; Standard Test Method for Air Permeability of Textile Fabrics). For the applications intended for the construction, the hydrostatic head or hydrohead is measured in terms of centimeters of water (with increasing resistance to passage therethrough of a column of water decreasing the air permeability), while the air permeability is measured in terms of cubic feet per minute per foot squared (with increasing passage of a volume of air therethrough decreasing the hydrostatic head). A hydrohead of 15 cms is considered to be more than adequate even for diaper applications, and, while any air permeability greater than zero represents an improvement over the plastic currently used in diapers, an air permeability of at least 10 CFM is considered desirable. While it is possible to achieve quite high air permeabilities (as high as 180 CFM), the corresponding hydroheads are quite low (even going below 15 cm).

EXAMPLE

In order to illustrate the manufacture of the materials of the present invention and their efficacy, various samples were created by applying a single meltblown layer to an SMS substrate to create a new barrier sheet.

The substrate was all polypropylene. A prefabricated polypropylene non-woven substrate construction having meltblown (M) and spunbond (S) fibers in a configuration of S-M-S at a level of 7-4-7 gsm was used as a base substrate material. The spunbond layers of the substrate were made from Exxon 3445, and the meltblown layer of the substrate was made from Montell 3495G resin.

The add-on (i.e., the polymer meltblown onto the substrate) was as follows:

Samples 18, 19 and 20: meltblown fibers of polypropylene (PP) (available under the trade name EXXON PD 3546G PP) were sprayed onto the SMS substrate to produce an SMSM construction.

Samples 21, 22 and 23: meltblown fibers of an 86/14 weight ratio copolymer of ethylene (e) and vinyl acetate (va) (the eva or EVA copolymer being available under the trade name EXXON MV02514 ESCORENE) were sprayed onto the SMS substrate to produce an SMSM construction. The melt index of this raw add-on material is 2500, and the ring and ball softening point is 88° C.

The meltblown layers of the substrate were all relatively coarse fibers, as was the meltblown layer of the add-on (as indicated in Table I). The meltblown polymer add-on was added to the substrate as a single layer.

Key parameters, such as the rate and amount of flow of meltblown resin through the meltblown die and the process temperatures of the die body and air, were adjusted to get fine micro denier fibers. The final meltblown fiber layer is the heaviest of all the different layers. The resultant SMSM fabric has a nice soft hand and the physical properties summarized in Table 1.

In Table I, for each sample, there is identified the weight of each component of the SMS substrate in grams per square meter (GSM) and the composition of the meltblown polymer and the weight thereof added in grams per square meter (GSM). Test results on each sample are provided (as an average of six different tests) and include machine strip tensile and horizontal or cross strip tensile (on 1 inch by 7 inch strips), trapezoidal tear strength (lbs.), weight in ounces per square yard (osy), fineness (thickness) in mils, air permeability in cubic feet per minute (cfm), and hydrostatic head in centimeters (cms). The hydrostatic head was measured by Poly-bond, Inc.'s "rising water column" test wherein water rises at 254 mm per minute, gradually increasing the pressure to a suspended specimen. The test continues until water penetrates the specimen.

In Table I, the percent CV is the Coefficient of Variation and equal to the standard deviation×100/mean.

Figure 10:
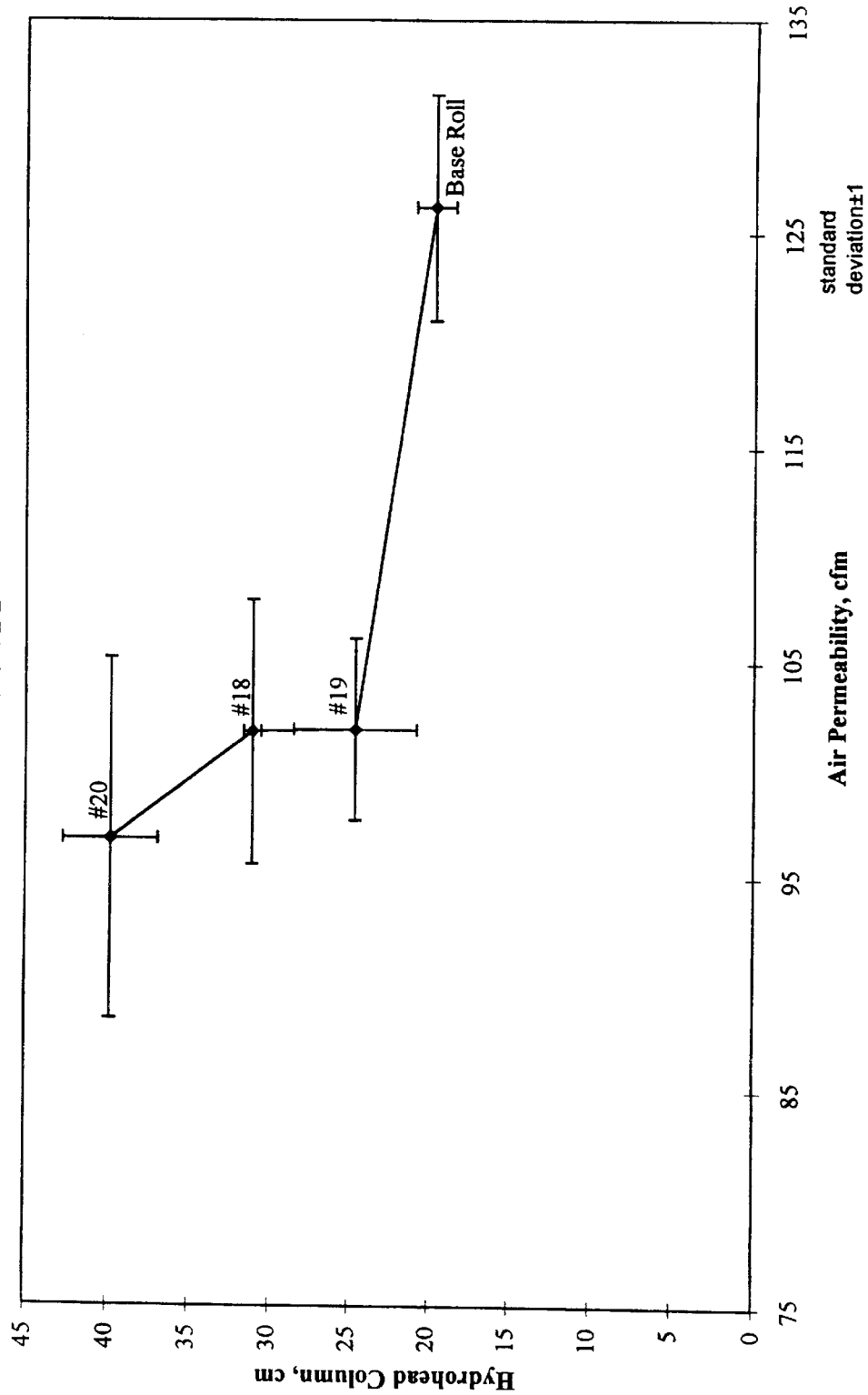
FIG. 10 is a graph showing the hydrohead column (i.e., the hydrostatic head) as a function of air permeability for the base SMS substrate and the three SMSM samples 18–20 having the add-on meltblown layer of polypropylene.
Figure 11:
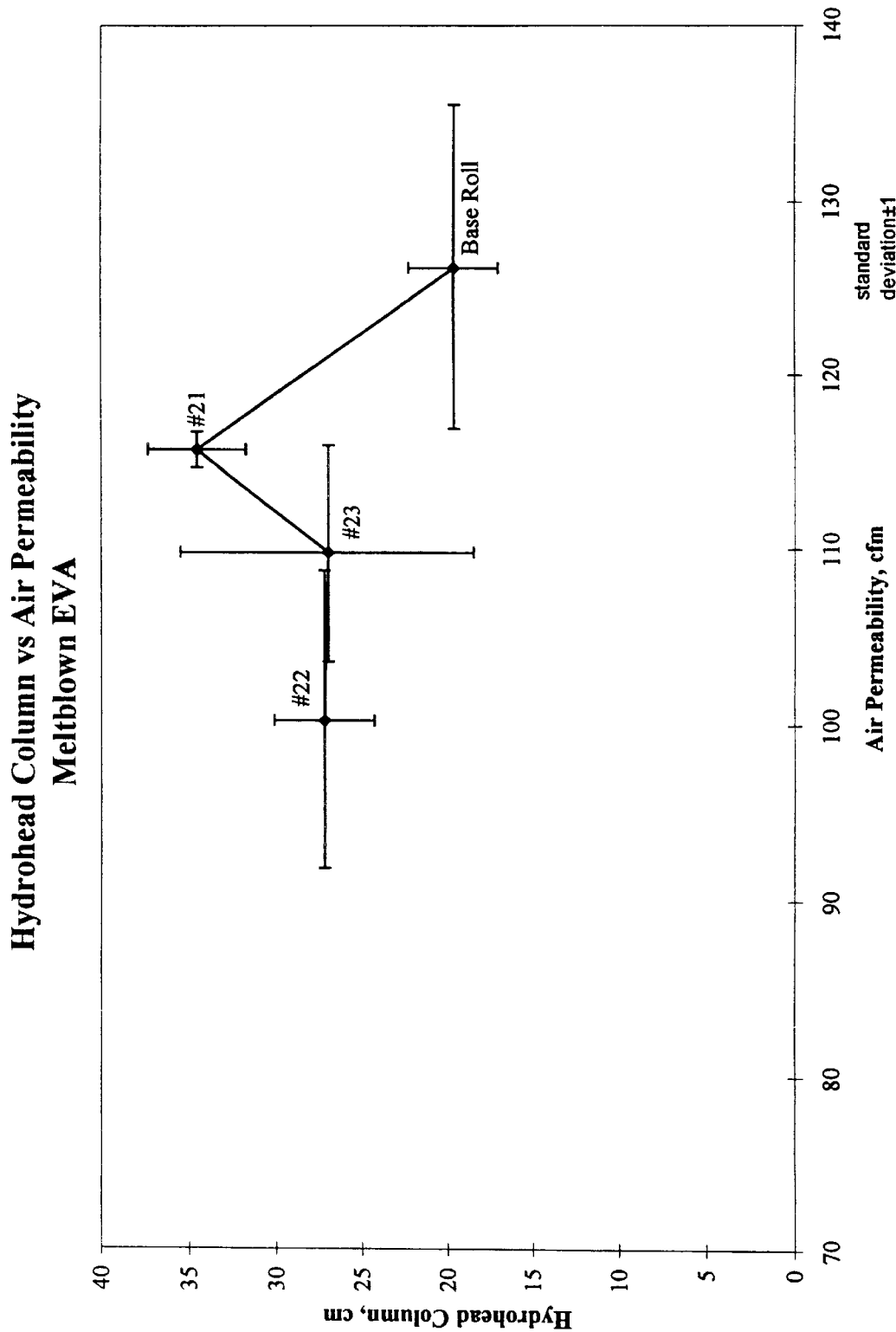
FIG. 11 is a graph similar to FIG. 10 for the base SMS substrate and the three SMSM samples 21–23 having the add-on meltblown layer of eva copolymer.
Figure 12:
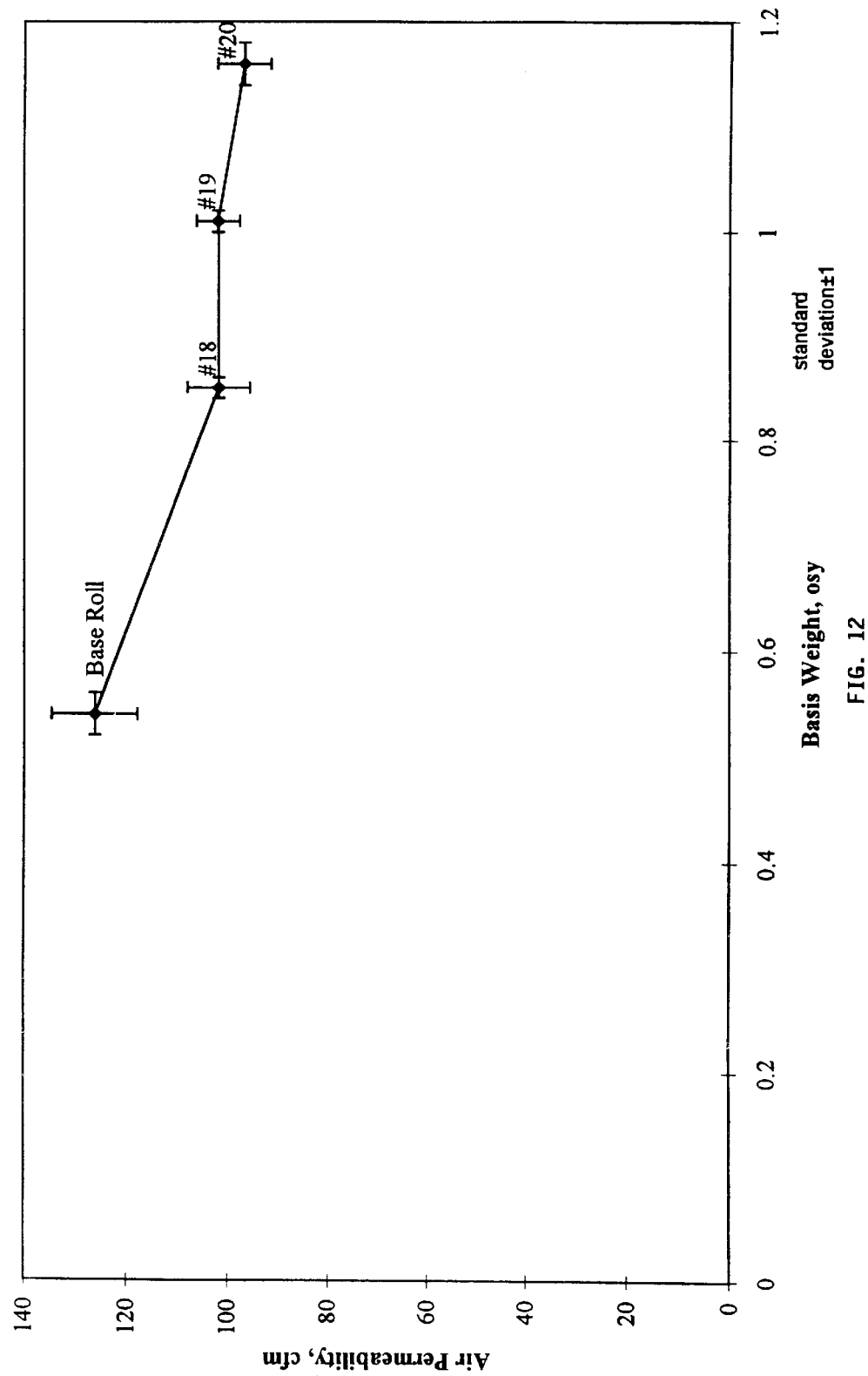
FIG. 12 is a graph showing the air permeability as a function of the basis weight for the base substrate and the three samples 18–20 having the add-on meltblown layer of polypropylene.
Figure 13:
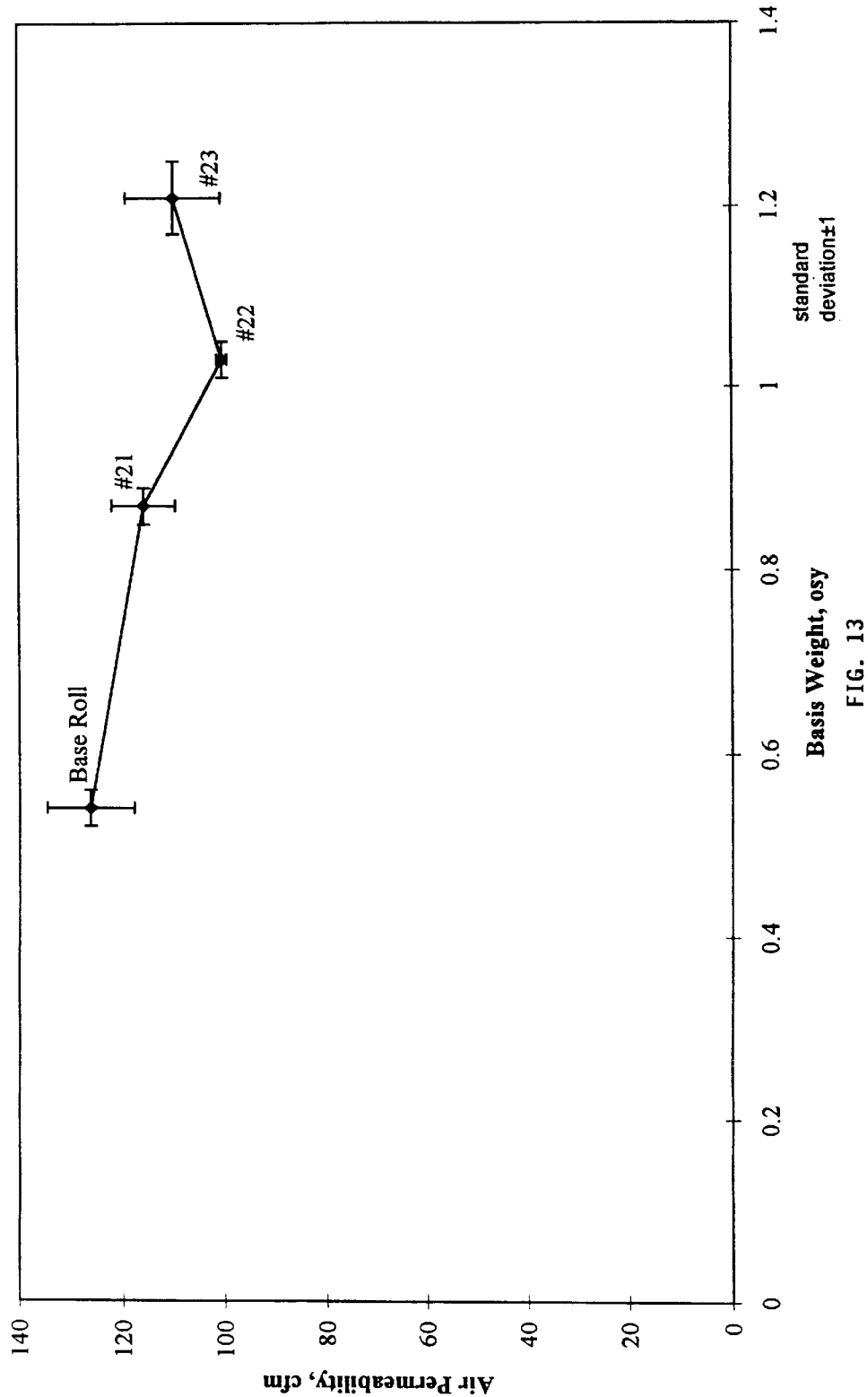
FIG. 13 is a graph similar to FIG. 12 for the base substrate and the three samples 21–23 having the add-on meltblown layer of eva copolymer.
Figure 14:
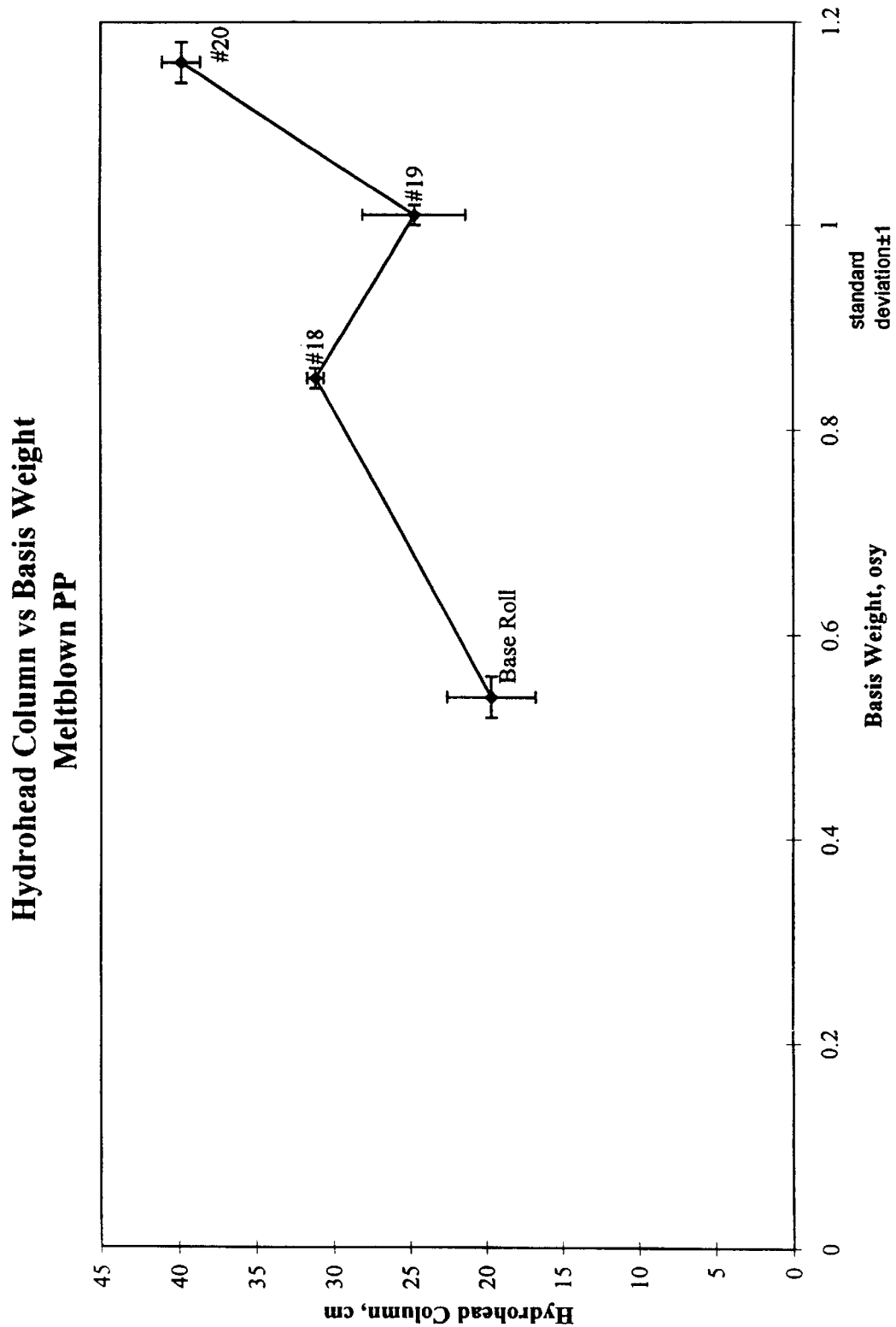
FIG. 14 is a graph showing the hydrohead column as a function of the basis weight for the base substrate and the three samples 18–20 having the add-on meltblown layer of polypropylene.
Figure 15:
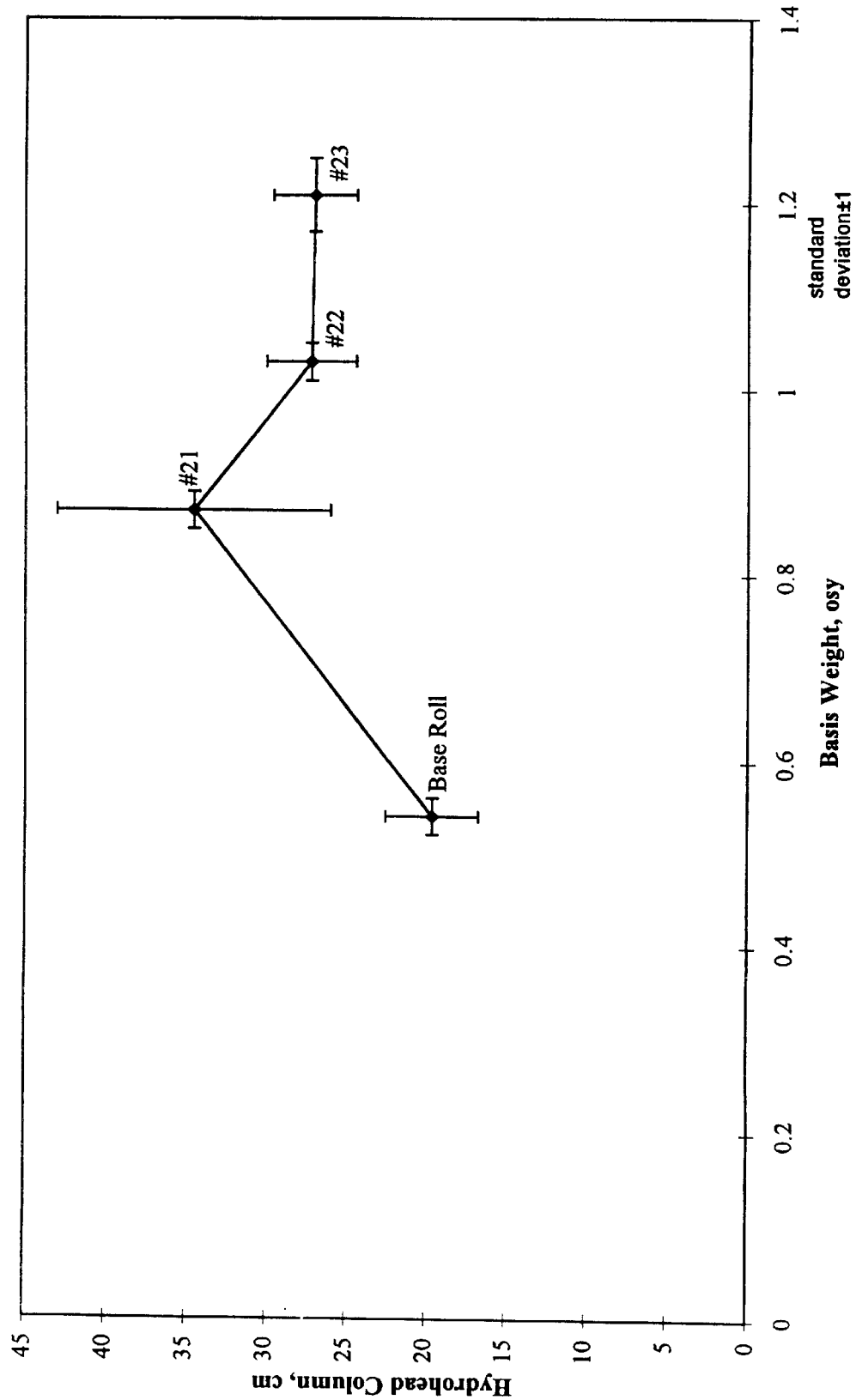
FIG. 15 is a graph similar to FIG. 14 for the base substrate and the three samples 21–23 having the add-on meltblown layer of eva copolymer.

Additionally, FIG. 10 shows the hydrohead column (i.e., the hydrostatic head) as a function of air permeability for the base SMS substrate and the three SMSM samples 18–20 having the add-on meltblown layer of polypropylene, while FIG. 11 is a similar graph for the base SMS substrate and the three SMSM samples 21–23 having the add-on meltblown layer of eva copolymer. FIG. 12 shows the air permeability as a function of the basis weight for the base substrate and the three samples 18–20 having the add-on meltblown layer of polypropylene, while FIG. 13 is a similar graph for the base substrate and the three samples 21–23 having the add-on meltblown layer of eva copolymer. FIG. 14 shows the hydrohead column as a function of the basis weight for the base substrate and the three samples 18–20 having the add-on meltblown layer of polypropylene, while FIG. 15 is a similar graph for the base substrate and the three samples 21–23 having the add-on meltblown layer of eva copolymer.

While the test results illustrate the relative merits of the base substrates and the various samples for use as a breathable diaper, feminine hygiene or like disposable sanitary product construction which is breathable and has an outer or backsheet surface which is cloth-like, each of the samples, as well as the base substrate, shows an acceptable air permeability of at least 10 CFM and an acceptable hydrostatic head of at least 15 cms.

Now that the preferred embodiments of the present invention have been shown and described in detail, various modifications and improvements thereon will become readily apparent to those skilled in the art. Accordingly, the spirit and scope of the present invention is to be interpreted broadly and limited only by the appended claims, and not by the foregoing specification.

TABLE I

| | Meltblown | | Tensile Strength - MD, g/cm | | Tensile Strength - CD, g/cm | | Weight, osy | | Thickness, mils | | Trapeziodal Tear Strength, lbs | |
|---|---|---|---|---|---|---|---|---|---|---|---|---|
| | Content, | | | | | | | | | | Max Ld.- | Max. Ld.- |
| ID | gsm | Resin | Average | St. Dev. | Average | St. Dev. | Average | St. Dev. | Average | St. Dev. | MD | CD |
| 7-4-7 | 4 | | 1159.07 | 115.84 | 432.83 | 43.67 | 0.54 | 0.02 | 40.67 | 4.5 | 8.05 | 4.89 |
| #18 | 10 | Exxon PD 3546G PP | 1102.14 | 96.45 | 484.58 | 56.96 | 0.85 | 0.01 | 82.5 | 6.8 | 8.13 | 5 |
| #19 | 15 | Exxon PD 3546G PP | 1248.25 | 77.88 | 561.28 | 49.21 | 1.01 | 0.01 | 93.83 | 4.88 | 7.9 | 4.98 |
| #20 | 20 | Exxon PD 3546G PP | 1415.99 | 82.45 | 603.18 | 43.37 | 1.16 | 0.02 | 111.5 | 5.09 | 8.93 | 4.88 |
| #21 | 10 | Exxon Escorene EVA MV02514 | 1056.14 | 90.6 | 379.6 | 53.89 | 0.87 | 0.02 | 6.08 | 0.6 | 7.18 | 4.96 |
| #22 | 15 | Exxon Escorene EVA MV02514 | 1070.69 | 85.93 | 407.14 | 32.67 | 1.03 | 0.02 | 75.33 | 12.64 | 6.7 | 4.55 |
| #23 | 20 | Exxon Escorene EVA MV02514 | 1025.1 | 58.65 | 407.17 | 32.31 | 1.21 | 0.04 | 9.15 | 0.78 | 6.8 | 5.45 |

| | Meltblown | | Air Permeability, cfm | | Hydrohead, cm | |
|---|---|---|---|---|---|---|
| | Content, | | | | | |
| ID | gsm | Resin | Average | St. Dev. | Average | St. Dev. |
| 7-4-7 | 4 | | 126.2 | 8.43 | 19.63 | 2.91 |
| #18 | 10 | Exxon PD 3546G PP | 101.78 | 6.17 | 31.07 | 0.55 |
| #19 | 15 | Exxon PD 3546G PP | 101.88 | 4.25 | 24.63 | 3.37 |
| #20 | 20 | Exxon PD 3546G PP | 96.75 | 5.29 | 39.8 | 1.23 |
| #21 | 10 | Exxon Escorene EVA MV02514 | 115.73 | 6.19 | 34.53 | 8.5 |
| #22 | 15 | Exxon Escorene EVA MV02514 | 100.3 | 1 | 27.2 | 2.8 |
| #23 | 20 | Exxon Escorene EVA MV02514 | 109.8 | 9.25 | 26.97 | 2.62 |

| | Fiber Size, microns | |
|---|---|---|
| ID | Average | % CV |
| #18 | 6.3 | 28 |
| #21 | 3.24 | 98 |

We claim:

1. A breathable disposable sanitary product construction having a cloth-like outer surface and including a plurality of materials comprising, from the skin-facing side outwardly:
   (A) a topsheet of liquid- and vapor-permeable hydrophilic material;
   (B) a core of highly absorbent material disposed outwardly of said topsheet for absorbing liquid received through said topsheet, said core having an inner surface in fluid communication with said topsheet and an outer surface;
   (C) a backsheet formed of a multilayer non-woven material which is hydrophobic and vapor-permeable for limiting the outward escape of liquid therethrough while enabling the outward escape of heat and water vapor therethrough, said backsheet being disposed at least partially as an outer surface of said diaper, said backsheet material having at least two meltblown layers and being a three-layer spunbond-meltblown-meltblown non-woven fabric consisting essentially of a spunbond layer and a plurality of meltblown layers disposed on an inner side of said spunbond layer.

2. A breathable disposable sanitary product construction having a cloth-like outer surface and including a plurality of materials comprising, from the skin-facing side outwardly:
   (A) a topsheet of liquid- and vapor-permeable hydrophilic material;
   (B) a core of highly absorbent material disposed outwardly of said topsheet for absorbing liquid received through said topsheet, said core having an inner surface in fluid communication with said topsheet and an outer surface;
   (C) a backsheet formed of a multilayer non-woven material which is hydrophobic and vapor-permeable for limiting the outward escape of liquid therethrough while enabling the outward escape of heat and water vapor therethrough, said backsheet being disposed at least partially as an outer surface of said diaper, said backsheet material having at least two meltblown layers and being a four-layer spunbond-meltblown-spunbond-meltblown non-woven fabric consisting essentially of two spunbond layers and two meltblown layers, one of said meltblown layers being disposed intermediate said two spunbond layers and bonding them together.

3. The construction of claim 2 wherein said backsheet material has the exterior meltblown layer formed from a polymer selected from the group of thermoplastic resins consisting of paraffin wax, polypropylene, and ethyl acetate copolymer.

4. A breathable disposable sanitary product construction having a cloth-like outer surface and including a plurality of materials comprising, from the skin-facing side outwardly:

(A) a topsheet of liquid- and vapor-permeable hydrophilic material;

(B) a core of highly absorbent material disposed outwardly of said topsheet for absorbing liquid received through said topsheet, said core having an inner surface in fluid communication with said topsheet and an outer surface;

(C) a backsheet formed of a multilayer non-woven material which is hydrophobic and vapor-permeable for limiting the outward escape of liquid therethrough while enabling the outward escape of heat and water vapor therethrough, said backsheet being disposed at least partially as an outer surface of said diaper, said backsheet material having at least two meltblown layers including a relatively coarse meltblown layer formed of fibers having a diameter of 3–5 microns and a relatively fine meltblown layer formed of fibers having a diameter of 0.5–1.5 microns.

5. The construction of claim 4 wherein said relatively fine meltblown layer is disposed inwardly of said relatively coarse meltblown layer.

6. The construction of claim 2 wherein said backsheet material has the exterior meltblown layer formed from a polymer selected from the group of thermoplastic resins consisting of paraffin wax, polypropylene, and ethyl vinyl acetate copolymer.

7. The construction of claim 2 wherein said backsheet material has the spunbond and interior meltblown layers thereof formed of polypropylene.

8. A breathable disposable sanitary product construction having a cloth-like outer surface and including a plurality of materials comprising, from the skin-facing side outwardly:

(A) a topsheet of liquid- and vapor-permeable hydrophilic material;

(B) a core of highly absorbent material disposed outwardly of said topsheet for absorbing liquid received through said topsheet, said core having an inner surface in fluid communication with said topsheet and an outer surface;

(C) a backsheet formed of a multilayer non-woven material which is hydrophobic and vapor-permeable for limiting the outward escape of liquid therethrough while enabling the outward escape of heat and water vapor therethrough, said backsheet being disposed at least partially as an outer surface of said diaper, said backsheet material having at least two meltblown layers and being one of:

(i) a three-layer spunbond-meltblown-meltblown non-woven fabric consisting essentially of a spunbond layer and a plurality of meltblown layers disposed on an inner side of said spunbond layer, and (ii) a four-layer spunbond-meltblown-spunbond-meltblown non-woven fabric consisting essentially of two spunbond layers and two meltblown layers, one of said meltblown layers being disposed intermediate said two spunbond layers and bonding them together.

9. The construction of claim 8 wherein said backsheet material has the exterior meltblown layer formed from a polymer selected from the group consisting of paraffin wax, polypropylene, ethyl vinyl acetate copolymer, and polypropylene/ethyl vinyl acetate copolymer, and the spunbond and interior meltblown layers thereof formed of polypropylene.

10. The construction of claim 8 formed exclusively of polypropylene.

11. A breathable disposable sanitary product construction having a cloth-like outer surface and including a plurality of materials comprising, from the skin-facing side outwardly:

(A) a topsheet of liquid- and vapor-permeable hydrophilic material;

(B) a core of highly absorbent material disposed outwardly of said topsheet for absorbing liquid received through said topsheet, said core having an inner surface in liquid communication with said topsheet and an outer surface;

(C) a barrier formed of a multilayer non-woven material which is hydrophobic and vapor-permeable for limiting the outward escape of liquid therethrough while enabling the outward escape of heat and water vapor therethrough, said barrier having a base disposed adjacent said core outer surface; and (D) a backsheet formed of a multilayer non-woven material which is hydrophobic and vapor permeable for limiting the outward escape of liquid therethrough while enabling the outward escape of heat and water vapor therethrough, said backsheet being disposed at least partially as an outer surface of said diaper;

at least one of said barrier material and said backsheet material having at least two meltblown layers.

12. The construction of claim 11 wherein said barrier material is a three-layer spunbond-meltblown-meltblown non-woven fabric formed of a spunbond layer and a plurality of meltblown layers disposed on an inner side of said spunbond layer, and.

13. The construction of claim 11 wherein said barrier material is a four-layer spunbond-meltblown-spunbond-meltblown non-woven fabric formed of two spunbond layers and two meltblown layers, one of said meltblown layers being disposed intermediate said two spunbond layers and bonding them together.

14. The construction of claim 11 wherein said barrier material includes a relatively coarse meltblown layer formed of fibers having a diameter of 3–5 microns and a relatively fine meltblown layer formed of fibers having a diameter of 0.5–1.5 microns.

15. The construction of claim 14 wherein said relatively fine meltblown layer is disposed inwardly of said relatively coarse meltblown layer.

16. The construction of claim 11 wherein said barrier material has the exterior meltblown layer formed from a polymer selected from the group consisting of paraffin wax, polypropylene, and ethyl vinyl acetate copolymer.

17. The construction of claim 11 wherein said barrier material has the spunbond and interior meltblown layers thereof formed of polypropylene.

18. The construction of claim 11 wherein each of said materials having at least two meltblown layers is a three-layer spunbond-meltblown-meltblown non-woven fabric formed of a spunbond layer and a plurality of meltblown layers disposed on an inner side of said spunbond layer.

19. The construction of claim 11 wherein each of said materials having at least two meltblown layers is a four-layer spunbond-meltblown-spunbond-meltblown non-woven fabric formed of two spunbond layers and two meltblown layers, one of said meltblown layers being disposed intermediate said two spunbond layers and bonding them together.

20. The construction of claim 11 wherein each of said materials having at least two meltblown layers includes a relatively coarse meltblown layer formed of fibers having a diameter of 3–5 microns and a relatively fine meltblown layer formed of fibers having a diameter of 0.5–1.5 microns.

21. The construction of claim 20 wherein, in each of said materials having at least two meltblown layers, said relatively fine meltblown layer is disposed inwardly of said relatively coarse meltblown layer.

22. The construction of claim 11 wherein each of said materials having at least two meltblown layers has the exterior meltblown layer formed from a polymer selected from the group consisting of paraffin wax, polypropylene, and ethyl vinyl acetate copolymer.

23. The construction of claim 11 wherein each of said materials having at least two meltblown layers has the spunbond and interior meltblown layers thereof formed of polypropylene.

24. A breathable disposable sanitary product construction having a cloth-like outer surface and including a plurality of materials comprising, from the skin-facing side outwardly:
   (A) a topsheet of liquid- and vapor-permeable hydrophilic material;
   (B) a core of highly absorbent material disposed outwardly of said topsheet for absorbing liquid received through said topsheet, said core having an inner surface in fluid communication with said topsheet and an outer surface;
   (C) a barrier formed of a multilayer non-woven material which is hydrophobic and vapor-permeable for limiting the outward escape of liquid therethrough while enabling the outward escape of heat and water vapor therethrough, said barrier having a base disposed adjacent said core outer surface; and
   (D) a backsheet formed of a multilayer non-woven material which is hydrophobic and vapor permeable for limiting the outward escape of liquid therethrough while enabling the outward escape of heat and water vapor therethrough, said backsheet being disposed at least partially as an outer surface of said diaper;
   at least one of said barrier material and said backsheet material having at least two meltblown layers and being one of:
   (i) a three-layer spunbond-meltblown-meltblown non-woven fabric formed of a spunbond layer and a plurality of meltblown layers disposed on an inner side of said spunbond layer, and
   (ii) a four-layer spunbond-meltblown-spunbond-meltblown non-woven fabric formed of two spunbond layers and two meltblown layers, one of said meltblown layers being disposed intermediate said two spunbond layers and bonding them together.

25. The construction of claim 24 wherein said barrier material includes a relatively coarse meltblown layer formed of fibers having a diameter of 2–5 microns and a relatively fine meltblown layer formed of fibers having a diameter of 0.5–1.5 microns, said relatively fine meltblown layer being disposed inwardly of said relatively coarse meltblown layer; said barrier material having the exterior meltblown layer formed from a polymer selected from the group consisting of paraffin wax, polypropylene, and ethyl vinyl acetate, and the spunbond and interior meltblown layers thereof formed of polypropylene.

26. The construction of claim 24 wherein each of said barrier and backsheet materials has at least two meltblown layers and is one of
   (i) a three-layer spunbond-meltblown-meltblown non-woven fabric formed of a spunbond layer and a plurality of meltblown layers disposed on an inner side of said spunbond layer, and
   (ii) a four-layer spunbond-meltblown-spunbond-meltblown non-woven fabric formed of two spunbond layers and two meltblown layers, one of said meltblown layers being disposed intermediate said two spunbond layers and bonding them together;
   the exterior meltblown layer being formed from a polymer selected from the group consisting of paraffin wax, polypropylene, and ethyl vinyl acetate copolymer, and the spunbond and interior meltblown layers thereof formed of polypropylene.

27. A barrier sheet comprising a multilayer non-woven material having a cloth-like outer surface and which is hydrophobic and vapor-permeable for limiting the outward escape of fluid therethrough while enabling the outward escape of heat and water vapor therethrough;
   said barrier sheet material having at least two meltblown layers and being one of:
   (i) a three-layer spunbond-meltblown-meltblown non-woven fabric formed of a spunbond layer and a plurality of meltblown layers disposed on one side of said spunbond layer, and
   (ii) a four-layer spunbond-meltblown-spunbond-meltblown non-woven fabric formed of two spunbond layers and two meltblown layers, one of said meltblown layers being disposed intermediate said two spunbond layers and bonding them together;
   said barrier sheet material including a relatively coarse meltblown layer formed of fibers having a diameter of 3–5 microns and a relatively fine meltblown layer formed of fibers having a diameter of 0.5–1.5 microns, said relatively fine meltblown layer being disposed on one side of said relatively coarse meltblown layer.

28. The barrier sheet of claim 27 wherein said barrier sheet material includes a relatively coarse meltblown layer formed of fibers having a diameter of 3–5 microns and a relatively fine meltblown layer formed of fibers having a diameter of 0.5–1.5 microns, said relatively fine meltblown layer being disposed on one side of said relatively coarse meltblown layer.

29. The barrier sheet of claim 27 wherein said barrier sheet material has the exterior meltblown layer formed from a polymer selected from the group consisting of paraffin wax, polypropylene, and ethyl vinyl acetate copolymer, and the spunbond and interior meltblown layers thereof formed of polypropylene.

30. A breathable disposable sanitary product construction including a plurality of materials comprising, from the skin-facing side outwardly:
   (A) a topsheet of liquid- and vapor-permeable hydrophilic material;
   (B) a core of highly absorbent material disposed outwardly of said topsheet for absorbing liquid received through said topsheet, said core having an inner surface in fluid communication with said topsheet and an outer surface;
   (C) a barrier formed of a multilayer non-woven material which is hydrophobic and vapor-permeable for limiting the outward escape of liquid therethrough while enabling the outward escape of heat and water vapor therethrough, said barrier having a base disposed adjacent said core outer surface; and
   (D) a backsheet formed of a multilayer non-woven material which is hydrophobic and vapor permeable for limiting the outward escape of liquid therethrough while enabling the outward escape of heat and water vapor therethrough, said backsheet being disposed at least partially outwardly of said barrier base.

31. The construction of claim 30 wherein said backsheet material is a two-layer spunbond-meltblown non-woven fabric formed of a spunbond layer and a meltblown layer.

32. The construction of claim 30 wherein said backsheet material is a three-layer spunbond-meltblown-spunbond non-woven fabric formed for two spunbond layers and a meltblown layer disposed intermediate said spunbond layers and bonding them together.

33. The construction of claim 30 including an additive or coating which increases the hydrophobicity of said backsheet material.

34. The construction of claim 30 wherein a portion of said backsheet material includes elastic material such that, in use, a portion of said backsheet material is gathered about the legs of the user.

35. The construction of claim 30 wherein said barrier material is a two-layer spunbond-meltdown non-woven fabric formed of a spunbond layer and a meltblown layer.

36. The construction of claim 30 wherein said barrier material is a three-layer spunbond-meltblown-spunbond non-woven fabric formed of two spunbond layers and a meltblown layer disposed intermediate said spunbond layer and bonding them together.

37. The construction of claim 30 including an additive or coating which increases the hydrophobicity of said barrier material.

38. The construction of claim 30 wherein said topsheet is a one-layer spunbond non-woven material.

39. The construction of claim 30 wherein said topsheet is formed of a liquid-distributing material.

40. The construction of claim 30 wherein said topsheet is a two-layer fabric formed of an inner layer of a liquid and vapor permeable hydrophilic non-woven material and an outer layer of a liquid-distributing material.

41. The construction of claim 30 which includes a hydrophobic enhancer formed of a multilayer non-woven material which is hydrophobic and vapor-permeable for limiting the outward escape of liquid therethrough while enabling the outward escape of heat and water vapor therethrough, said hydrophobic enhancer being disposed at least partially outwardly of said barrier based and inwardly of said backsheet.

42. The construction of claim 41 in which said hydrophobic enhancer is a two-layer spunbond-meltblown non-woven fabric formed of a spunbond layer and a meltblown layer.

43. The construction of claim 41 in which said hydrophobic enhancer is a three-layer spunbond-meltblown-spunbond non-woven fabric formed of two spunbond layers and a meltblown layer disposed intermediate said spunbond layer and bonding them together.

44. The construction of claim 30 including a hydrophobic coating disposed adjacent an inner surface of said backsheet.

45. The construction of claim 44 wherein said coating is cracked or fractured to provide breathability thereto.

46. The construction of claim 45 wherein said cracked coating is polymeric.

47. The construction of claim 45 wherein said cracked coating is an ethyl vinyl acetate (EVA) extrusion having cracks or fractures sufficient to provide breathability thereto.

48. The construction of claim 30 wherein said core also has two lateral side surfaces and in use said barrier has a U-shaped configuration with a pair of flanges upstanding from said barrier base, each said flange extending inwardly adjacent to a respective one of said core lateral side surface.

49. The construction of claim 48 wherein said barrier base is thicker than said barrier flanges to further limit the outward escape of liquid therethrough.

50. The construction of claim 48 wherein a portion of said barrier flanges includes elastic material such that in use a portion of said barrier flanges are gathered about the legs of the user.

51. The construction of claim 48 wherein said barrier flanges are contiguous to said core lateral side surfaces.

52. The construction of claim 48 wherein said topsheet defines a topsheet base disposed adjacent said core inner surface and a pair of topsheet flanges extending from said topsheet flange being secured to a respective barrier flange.

53. A breathable disposable sanitary product construction including a plurality of materials comprising, from the skin-facing said outwardly:

(A) a vapor-permeable topsheet of hydrophilic, liquid-distributing, non-woven material, said topsheet including an inner layer of hydrophilic non-woven material and an outer layer of liquid-distributing material;

(B) a core of highly absorbent material disposed outwardly of said topsheet for absorbing liquid received through said topsheet, said core having an inner surface in fluid communication with said topsheet, an outer surface and two lateral side surfaces;

(C) a hydrophobic and vapor-permeable barrier formed of a three-layer spunbond-meltblown-spunbond non-woven fabric formed of two spunbond layers and a meltblown layer disposed intermediate said spunbond layers and bonding them together, for limiting the outward escape of liquid therethrough while enabling the outward escape of heat and water vapor therethrough, in use said barrier being in a U-shaped configuration having a base disposed adjacent said core outer surface and a pair of flanges upstanding from said base and each extending inwardly adjacent to a respective one of said core lateral side surfaces;

(D) a vapor-permeable hydrophobic enhancer formed of a three-layer spunbond-meltblown-spunbond non-woven fabric formed of two spunbond layers and a meltblown layer disposed intermediate said spunbond layers and bonding them together, for limiting the outward escape of heat and water vapor therethrough, said enhancer being disposed at least partially outwardly of said barrier; and (E) a hydrophobic and vapor-permeable backsheet formed of a three-layer spunbond-meltblown-spunbond non-woven fabric formed of two spunbond layers and a meltblown layer disposed intermediate said spunbond layers and bonding them together, for limiting the outward escape of liquid therethrough while enabling the outward escape of heat and water vapor therethrough, said backsheet being disposed at least partially outwardly of said enhancer.

54. The construction of claim 2 wherein said backsheet material has the spunbond and interior meltblown layers thereof formed of polypropylene.

* * * * *